(12) United States Patent
Jou et al.

(10) Patent No.: US 11,510,565 B2
(45) Date of Patent: Nov. 29, 2022

(54) DEVICE AND METHOD FOR SIMPLY DETERMINING MAXIMUM PERMISSIBLE EXPOSURE TIME OF RETINA

(71) Applicant: NATIONAL TSING HUA UNIVERSITY, Hsinchu (TW)

(72) Inventors: Jwo-Huei Jou, Hsinchu (TW); Jing-Hsiu Chen, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 310 days.

(21) Appl. No.: 17/028,794

(22) Filed: Sep. 22, 2020

(65) Prior Publication Data

US 2021/0353137 A1 Nov. 18, 2021

(30) Foreign Application Priority Data

May 13, 2020 (TW) ................................. 109115807

(51) Int. Cl.
*A61B 3/00* (2006.01)
*G06T 7/00* (2017.01)

(52) U.S. Cl.
CPC .......... *A61B 3/0025* (2013.01); *G06T 7/0012* (2013.01); *G06T 2207/30041* (2013.01)

(58) Field of Classification Search
CPC ................ A61B 3/0025; G06T 7/0012; G06T 2207/30041; G01J 1/4209
USPC ......................................................... 351/205
See application file for complete search history.

(56) References Cited

U.S. PATENT DOCUMENTS

2008/0231858 A1* 9/2008 Kayahara ............... G01N 21/57
356/445
2010/0053346 A1* 3/2010 Mitsunaga ......... H04N 5/23254
348/208.6

* cited by examiner

*Primary Examiner* — Mohammed A Hasan

(57) ABSTRACT

A device for simply determining maximum permissible exposure time (MPE) of retina is disclosed, which principally comprises a light receiving unit and a core processor that is provided with a color temperature determining unit, a luminous flux determining unit and a calculating unit therein. The color temperature determining unit and the luminous flux determining unit are configured for completing a color temperature determination and a luminous flux determination of a light provided by a light source, respectively. The calculating unit is configured for calculating a maximum permissible exposure time (MPE) of retina of the light source based on a use distance and a color temperature and a luminous flux of the light. By using this device, generic users are facilitated to achieve the calculation of any one kind of light's MPE by themselves, without needing to using any spectrometer.

18 Claims, 8 Drawing Sheets

DEVICE AND METHOD FOR SIMPLY DETERMINING MAXIMUM PERMISSIBLE EXPOSURE TIME OF RETINA

BACKGROUND OF THE INVENTION

1. Field of the Invention

The present invention relates to the technology field of MPE (maximum permissible exposure time of retina) calculating, and more particularly to a device and method for simply determining maximum permissible exposure time of retina.

2. Description of the Prior Art

It is well known that natural light consists of visible and invisible lights, wherein infrared (IR) light and ultraviolet (UV) light are two of the invisible lights. On the other hand, it is understood that the visible lights comprise red, orange, yellow, green, blue, indigo, and purple lights. Retina is an important part of human eyes, and has specific function of converting light signal to neural signal. FIG. 1 illustrates one diagram for showing a sunlight spectrum, and there is another one diagram for showing an emission spectrum of a white light LED provided in FIG. 2. It is known that, the specific light irradiated from sun commonly has a continuous spectrum. Differing from the sunlight, however, an LED lighting element that is configured for emitting an artificial light (i.e., white light) has been widely applied in various illumination devices, backlight modules and self-luminous display panels. From FIG. 2, it is also found that the white light emitted by the LED lighting element has a discontinuous spectrum that merely contains visible wavelengths in a range from 430 nm to 680 nm. Moreover, FIG. 1 also indicates that the intensity of the green light is greater than that of the blue light in the sunlight spectrum. On the contrary, however, FIG. 2 shows that the artificial LED light specifically contains a high-intensity blue light.

As explained in more detail below, blue light contains a visible wavelength in a range between 400 nm and 500 nm, and a proper lighting of blue light can lift a person's spirits and make the person has a feeling of pleasure. However, many different research reports all conclude that, too much illumination of blue light would bring light pollution, disturbance of human biological clock, loss of sleep, and eye damage on. To be more seriously, too much illumination of blue light may cause a man suffer from macular degeneration. Therefore, since FIG. 2 has showed that the artificial LED light specifically contains the blue light with high-intensity as well as that people every day have a considerably long elapsed time of using their 3C products (like laptop computer, smart phone or tablet PC) in every day, ophthalmologist, eyewear manufacturing companies and lamp manufacturing companies have made great efforts to propaganda the important issue of blue light hazard.

Blue light is the part of the spectrum with the highest energy content and that still can reach the retina. It has been studied that, photochemical means that due to the high energy content of the incoming light some chemical reactions take place on the retina, eventually bringing photoretinitis on, which is a retinal lesion induced by light, in particular the high-energy blue light. Herein, it needs to explain that, how to calculate a specific light's maximum permissible exposure (MPE) limit for retina has been disclosed in American National Standards Institute (ANSI) Z136.1-1. Nowadays, MPE limit is usually expressed in terms of the allowable exposure time (in seconds) for a given irradiance (in watts/cm$^2$) at a particular wavelength. Therefore, a specific light's MPE limit value would grow with the increase of the illuminance thereof. Of course, the MPE limit of a short-wavelength light is certainly higher than that of a long-wavelength light in case of the forgoing two lights being modulated to have the same illuminance.

Briefly speaking, when calculating a specific light's MPE limit value, it needs to use a spectrometer to collect a spectrum data of the specific light, and then obtaining corresponding spectral weighting value by looking up a blue-light hazard function. Consequently, after using the mathematical formulas provided by ANSI to calculate effective radiance ($L_B$) and effective irradiance ($E_B$), numeric value of the MPE limit of the specific light would be therefore calculated.

The unit of the forgoing maximum permissible exposure (MPE) limit is "second", such that the MPE limit is also called as MPE time or MPE. In other words, MPE is adopted for describing a maximum endurance time of retina for a specific light such as a light provided by a desk lamp. However, for generic users, it is unlikely for them to purchase a spectrometer in order to collect spectrum data for further achieving the calculation of a specific light's MPE.

From above descriptions, it is clear that there is a lack of a device for helping generic users in the calculation of MPE of any one kind of light. In view of that, inventors of the present application have made great efforts to make inventive research and eventually provided a device and method for simply determining maximum permissible exposure time of retina.

SUMMARY OF THE INVENTION

The primary objective of the present invention is to disclose a device and method for simply determining maximum permissible exposure time (MPE) of retina. The device principally comprises a light receiving unit and a core processor. Particularly, there are a color temperature determining unit, a luminous flux determining unit and a calculating unit provided in the core processor. After the light receiving unit receives an illumination light from a light source, the color temperature determining unit and the luminous flux determining unit complete a color temperature determination and a luminous flux determination of the illumination light, respectively. After that, the calculating unit is able to consequently calculate a maximum permissible exposure time (MPE) of retina of the light source based on a use distance, a value of color temperature transmitted from the color temperature determining unit and a value of luminous flux received from the luminous flux determining unit.

As such, by using this novel device, generic users are facilitated to achieve the calculation of any one kind of light's MPE by themselves, without needing to collect spectrum data, and also without needing to look up a blue-light hazard function in order to obtain corresponding spectral weighting value.

In order to achieve the primary objective of the present invention, inventors of the present invention provides an embodiment for the device for simply determining maximum permissible exposure time of retina, comprising:

a light receiving unit, being used for receiving a specific light that is irradiated from a light source, wherein there is a use distance between the light receiving unit and the light source; and a core processor, being coupled to the light receiving unit for receiving the specific light, and comprising:
  a color temperature determining unit for completing a color temperature determination of the specific light;
  a luminous flux determining unit for carrying out a luminous flux determination of the specific light; and
  a calculating unit, being configure for calculating a maximum permissible exposure time (MPE) of the specific light based on the use distance and a color temperature and a luminous flux of the specific light.

In one embodiment, the forgoing device further comprises:
a distance sensing unit, comprising a data processor and a distance sensor that is selected from the group consisting of optical distance sensor, ultrasonic distance sensor, and radar distance sensor.

In one embodiment, the forgoing device further comprises:
a display unit, being coupled to the core processor, thereby being controlled by the core processor so as to display the use distance, the color temperature, the luminous flux, and/or the MPE;
an input unit, being coupled to the core processor, such that a user is facilitated to input the use distance to the core processor; and
a communication unit, being coupled to the core processor, such that the core processor is able to communicate with an external electronic device through the communication unit.

In one embodiment of the forgoing device, the calculating unit comprises a mathematical algorithm for completing a calculation of the MPE, and the mathematical algorithm being presented as $$MPE\left(\frac{F_L}{D}\right) = J + K\left(e^{\frac{-T}{L}}\right) + M\left(e^{\frac{-T}{N}}\right);$$

wherein MPE is the maximum permissible exposure time, $F_L$ being the luminous flux, D being the use distance, T being the color temperature, and J, K, L, M, and N being statistical experience constants.

In a practicable embodiment, the forgoing device is an electronic device selected from the group consisting of desk optical measuring instrument, portable optical measuring instrument, smartphone integrated with optical measuring unit, smartphone connected with external optical measuring module, tablet PC integrated with optical measuring unit, tablet PC connected with external optical measuring module, laptop computer integrated with external optical measuring unit, laptop computer connected with external optical measuring module, all-in-one desktop computer integrated with optical measuring unit, all-in-one desktop computer connected with external optical measuring module, and desktop computer connected with external optical measuring module.

In a practicable embodiment, the forgoing distance sensing unit comprises a data processor and a distance sensor that is selected from the group consisting of optical distance sensor, ultrasonic distance sensor, and radar distance sensor.

For achieving the primary objective of the present invention, inventors of the present invention also provides an embodiment for the method for simply determining maximum permissible exposure time of retina, comprising:
(1) letting a core processor be coupled to a light receiving unit;
(2) letting the light receiving unit receive a specific light that is irradiated from a light source, wherein there is a use distance between the light receiving unit and the light source;
(3) configuring a color temperature determining unit and a luminous flux determining unit in the core processor, so as to complete a color temperature determination and a luminous flux determination of the specific light; and
(4) configuring a calculating unit in the core processor, so as to carry out a calculation of a maximum permissible exposure time (MPE) of the specific light based on the use distance and a color temperature and a luminous flux of the specific light.

In one embodiment, the forgoing method further comprises:
(5) letting the core processor be coupled to a display unit, so as to control the display unit to show the use distance, the color temperature, the luminous flux, and/or the MPE.

In a practicable embodiment, the forgoing method is applied in an electronic device.

In a practicable embodiment, the use distance is inputted to the core processor by using an input unit.

In a practicable embodiment, the use distance is measured by a distance sensing unit comprising a data processor and a distance sensor that is selected from the group consisting of optical distance sensor, ultrasonic distance sensor, and radar distance sensor.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

To more clearly describe a device and method for simply determining maximum permissible exposure time of retina disclosed by the present invention, embodiments of the present invention will be described in detail with reference to the attached drawings hereinafter.

First Embodiment

Figure 1:
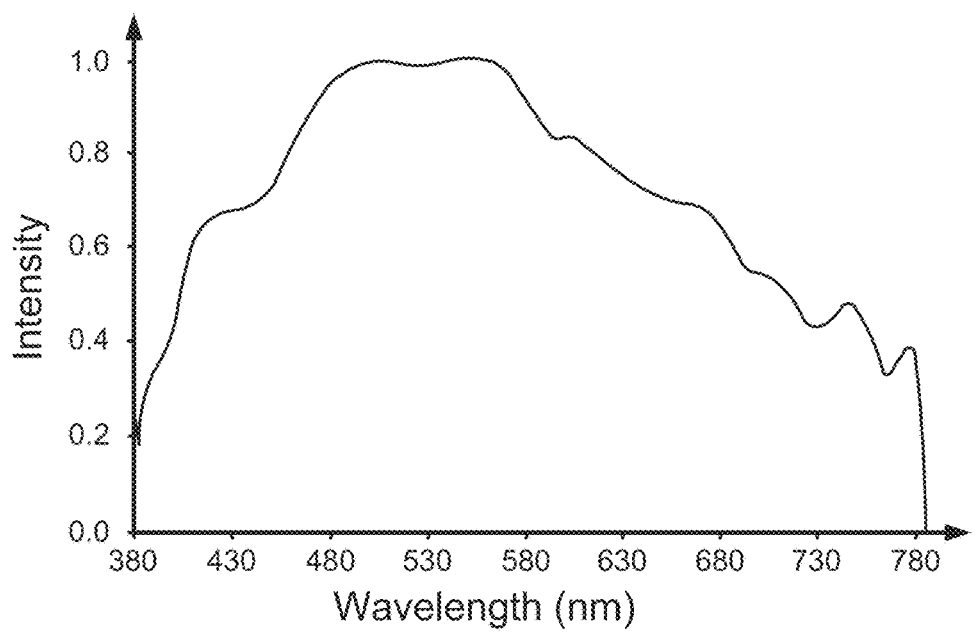
FIG. 1 shows a diagram for showing a sunlight spectrum.
Figure 2:
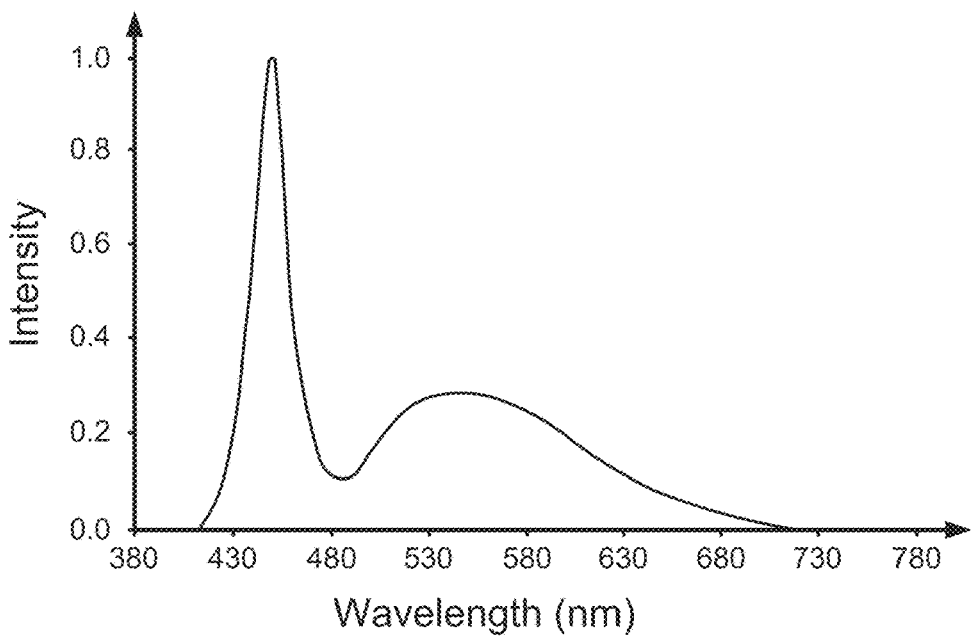
FIG. 2 shows a diagram for showing an emission spectrum of a white light LED.
Figure 3:
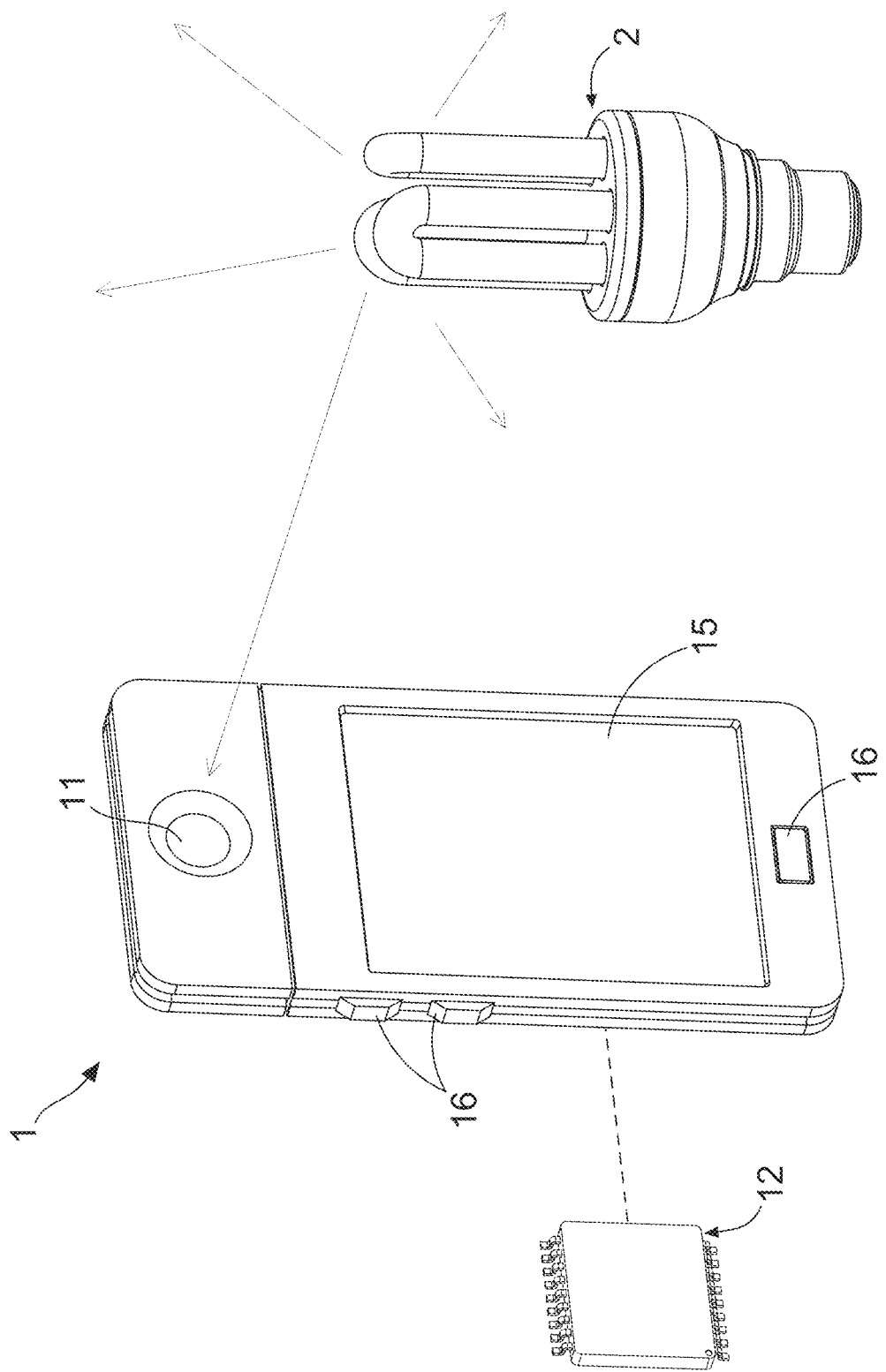
FIG. 3 shows a stereo diagram of a first embodiment of a device for simply determining maximum permissible exposure time (MPE) of retina according to the present invention.
Figure 4:
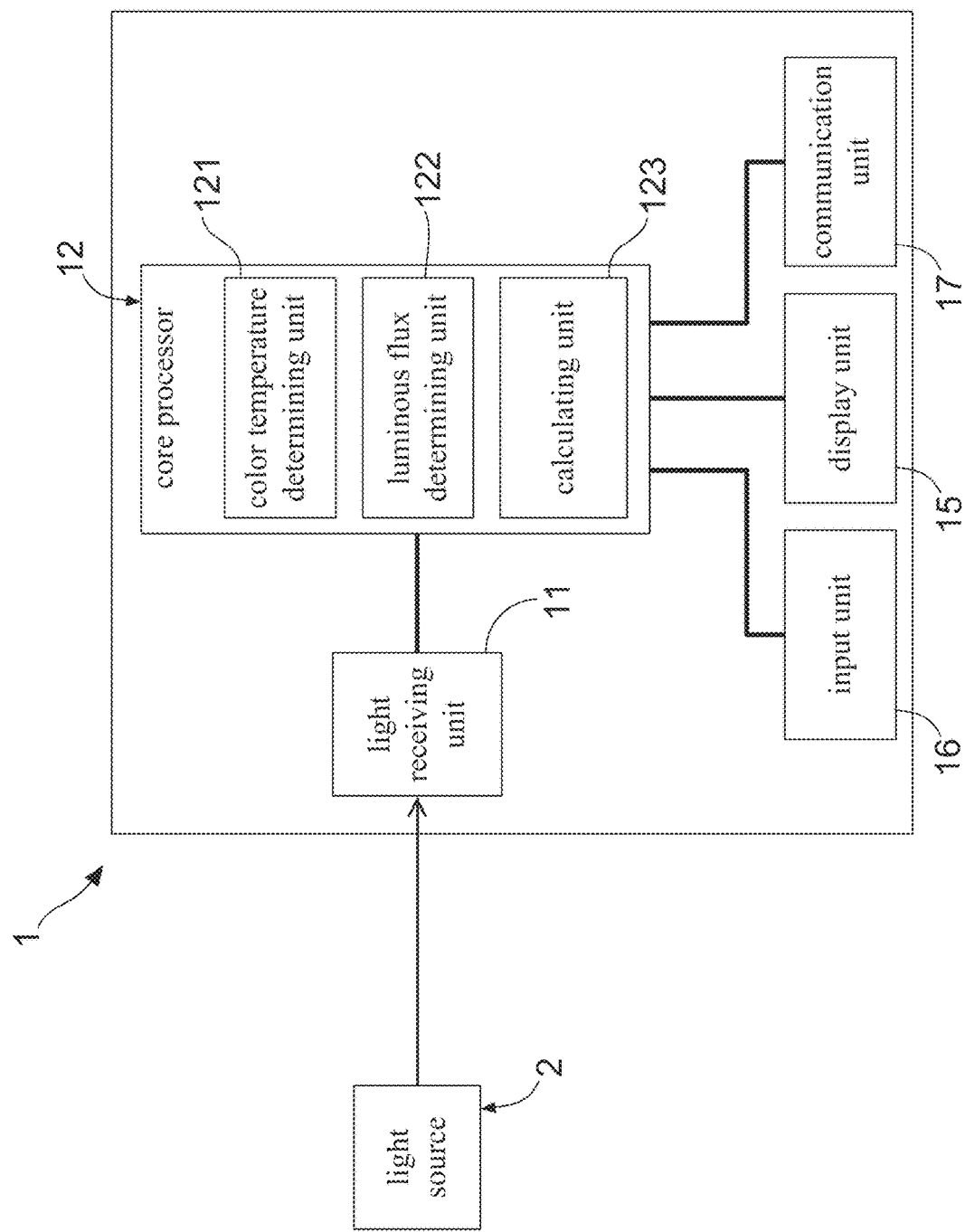
FIG. 4 shows a block diagram of the first embodiment of the device for simply determining MPE.

With reference to FIG. 3, there is shown a stereo diagram of a first embodiment of a device for simply determining maximum permissible exposure time (MPE) of retina according to the present invention. Moreover, FIG. 4 illustrates a block diagram of the first embodiment of the device for simply determining MPE. As FIG. 3 and FIG. 4 show, the device 1 for simply determining MPE of the present invention principally comprises a light receiving unit 11, a core processor 12, a display unit 15, and an input unit 16. In which, the light receiving unit 11 is disposed to having a use distance with a light source 2, thereby receiving a specific light irradiated from the light source 2 like an LED lighting fixture.

In first embodiment, the core processor 12 is coupled to the light receiving unit 11 for receiving the specific light. Particularly, there are a color temperature determining unit 121, a luminous flux determining unit 122 and a calculating unit 123 provided in the core processor 12, and the color temperature determining unit 121 and the luminous flux determining unit 122 are configured for completing a color temperature determination and a luminous flux determination of the specific light. Moreover, the calculating unit 123 is configure for calculating a maximum permissible exposure time (MPE) of the specific light based on the use distance and a color temperature and a luminous flux of the specific light. In a practicable embodiment, the forgoing color temperature determining unit 121, luminous flux determining unit 122 and calculating unit 123 can be are provided in the core processor 12 by a form of firmware, function library, application program, or operands.

In other words, the core processor 12 comprising the color temperature determining unit 121, the luminous flux determining unit 122 and the calculating unit 123 can be an application processor for being further integrated in an electronic device like the portable optical measuring instrument shown in FIG. 3. Besides the portable optical measuring instrument, moreover, the forgoing electronic device integrated with the core processor 12 can also be a desk optical measuring instrument, an instrument, a smartphone integrated with optical measuring unit, a smartphone connected with external optical measuring module, a tablet PC integrated with optical measuring unit, a tablet PC connected with external optical measuring module, a laptop computer integrated with external optical measuring unit, a laptop computer connected with external optical measuring module, an all-in-one desktop computer integrated with optical measuring unit, an all-in-one desktop computer connected with external optical measuring module, or a desktop computer connected with external optical measuring module.

As described in more detail below, the calculating unit 123 comprises a mathematical algorithm for completing a calculation of the MPE, and the present invention particularly designs the mathematical algorithm to be a mathematical equation of $$MPE\left(\frac{F_L}{D}\right) = J + K\left(e^{\frac{-T}{L}}\right) + M\left(e^{\frac{-T}{N}}\right).$$

In the forgoing mathematical equation, MPE is the maximum permissible exposure time, $F_L$ is the luminous flux, D is the use distance, T is the color temperature, and J, K, L, M, and N are statistical experience constants. It is worth noting that the five statistical experience constants are different from each other. Following Table (1) lists exemplary values for the five statistical experience constants.

TABLE 1

| Statistical experience constants | exemplary values |
| --- | --- |
| J | $1.85 \times 10^3$ |
| K | $1.29 \times 10^8$ |
| L | $2.81 \times 10^2$ |
| M | $2.29 \times 10^4$ |
| N | $3.49 \times 10^2$ |

Please refer to FIG. 3 and FIG. 4 again. In the first embodiment of the device 1, the display unit 15 is coupled to the core processor 12, thereby being controlled by the core processor 12 for displaying the use distance, the color temperature, the luminous flux, and/or the MPE. On the other hand, the input unit 16 is coupled to the core processor 12, such that a user is facilitated to input the use distance to the core processor 12. In a practicable embodiment, the display unit 15 is a touch screen display device, and the input unit 16 comprises a plurality of key presses. In addition, FIG. 3 and FIG. 4 also depict that a communication unit 17 is included in the device 1 of the present invention, and the communication unit 17 is coupled to the core processor 12, such that the core processor 12 is able to communicate with an external electronic device through the communication unit 17. The external electronic device can be a desk computer, a laptop computer, an all-in-one desk computer, a tablet PC, a cloud server, a smartphone, or a smart watch.

Figure 5:
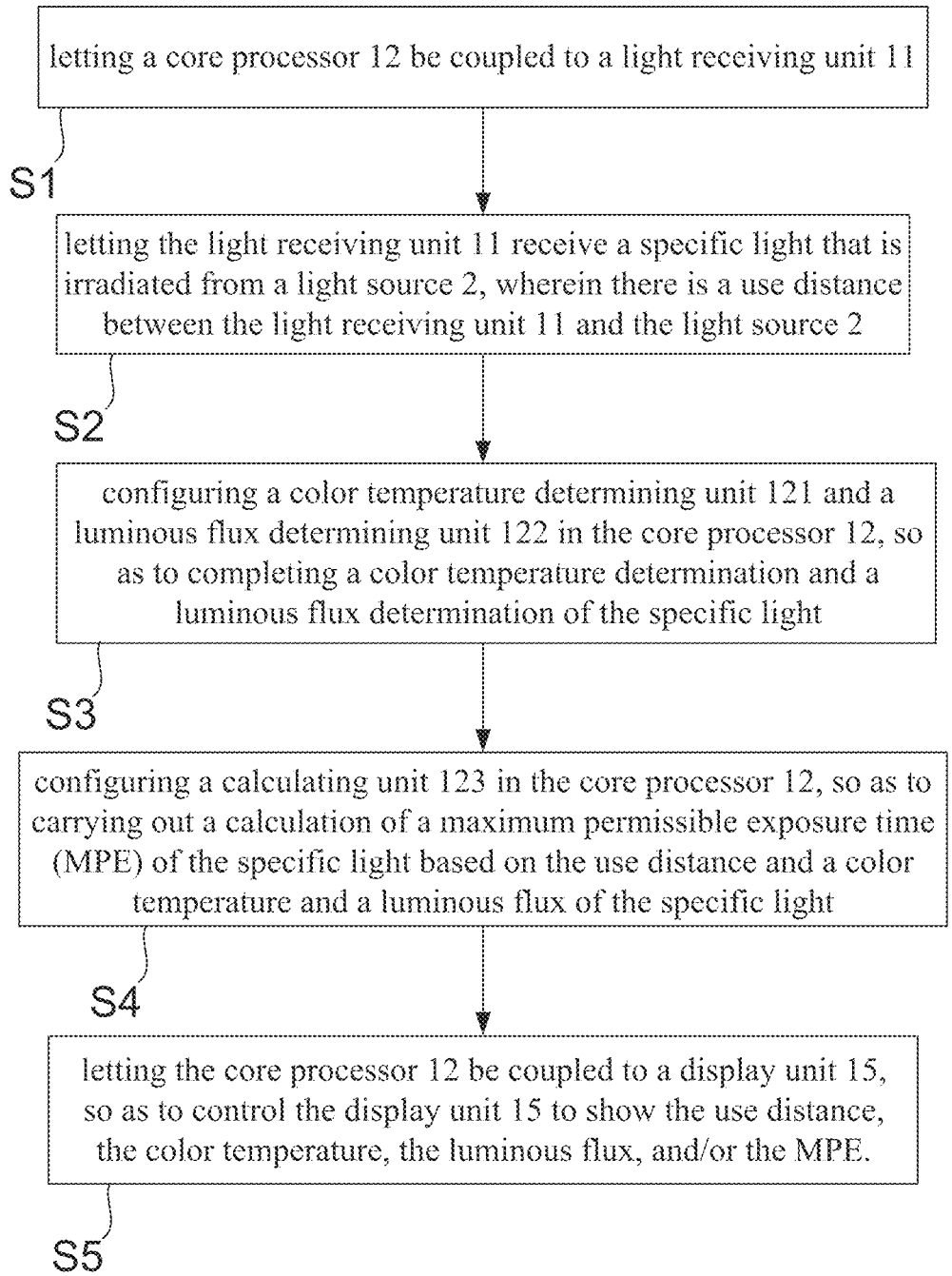
FIG. 5 shows a flowchart diagram of a method for simply determining MPE according to the present invention.

Moreover, the present invention also discloses a method for simply determining maximum permissible exposure time (MPE) of retina. From FIG. 3 and FIG. 4, it is understood that the method is applied in the core processor 12 that is integrated in an electronic device. FIG. 5 shows a flowchart diagram of a method for simply determining MPE according to the present invention. As FIG. 4 and FIG. 5 show, the method is firstly proceeded to steps S1 and S2, so as to let a core processor 12 be coupled to a light receiving unit 11, and let the light receiving unit 11 receive a specific light that is irradiated from a light source 2. It is noting that there is a use distance between the light receiving unit 11 and the light source 2. Next, the method is proceeded to step S3 for configuring a color temperature determining unit 121 and a luminous flux determining unit 122 in the core processor 12, so as to complete a color temperature determination and a luminous flux determination of the specific light. Subsequently, in step S4, a calculating unit 123 is configured in the core processor 12, so as to carry out a calculation of a maximum permissible exposure time (MPE) of the specific light based on the use distance and a color temperature and a luminous flux of the specific light. Consequently, the method is proceeded to step S5 for letting the core processor 12 be coupled to a display unit 15, so as to control the display unit 15 to show the use distance, the color temperature, the luminous flux, and/or the MPE.

Experiment

Figure 6:
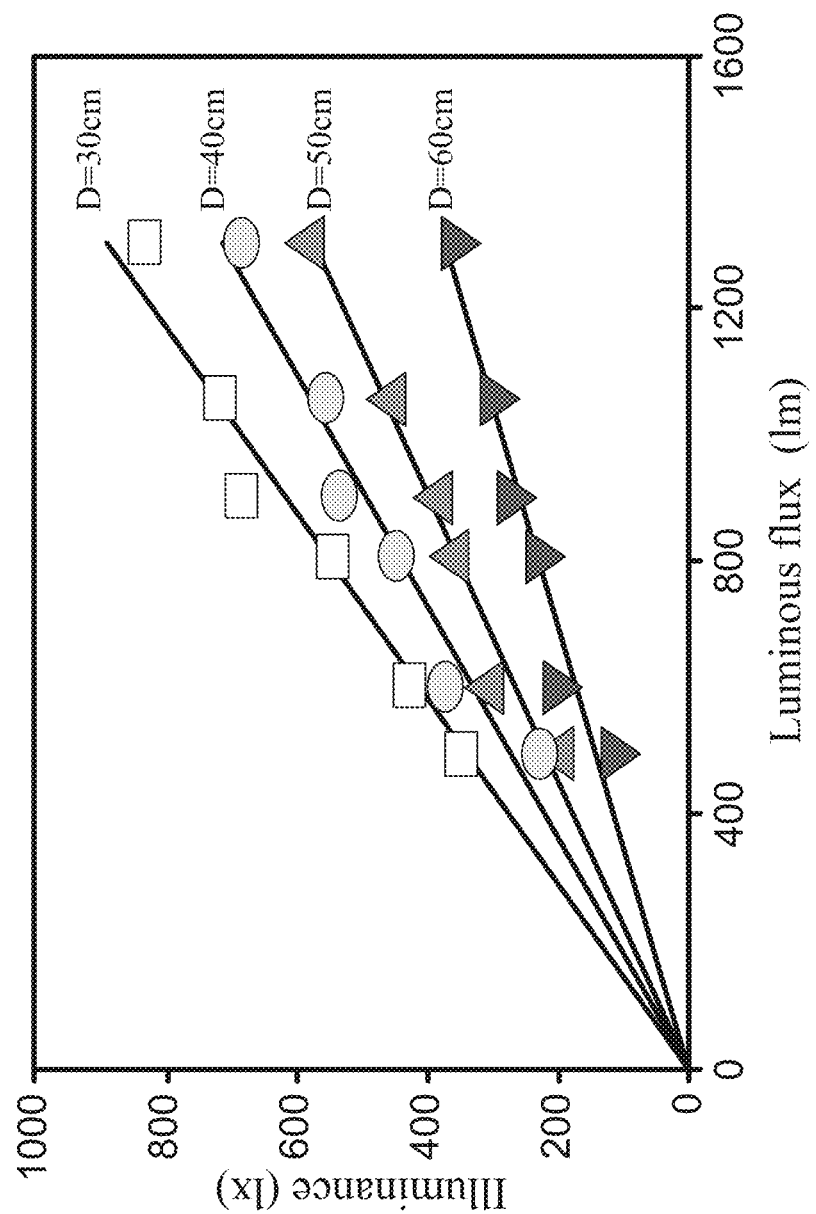
FIG. 6 shows a scatter plot of luminous flux versus illuminance.

Please refer to FIG. 6 showing a scatter plot of luminous flux versus illuminance. In FIG. 6, different values of the user distance of 30 cm, 40 cm, 50 cm, and 60 cm are particularly marked. From the experimental data of FIG. 6, it is easily found that the specific light's luminous flux grows with the increase of the illuminance thereof in case of the use distance is fixed to be a constant. On the other hand, in case of the luminous flux is fixed to be a constant, the specific light's illuminance decreases with the elongation of the use distance.

Figure 7:
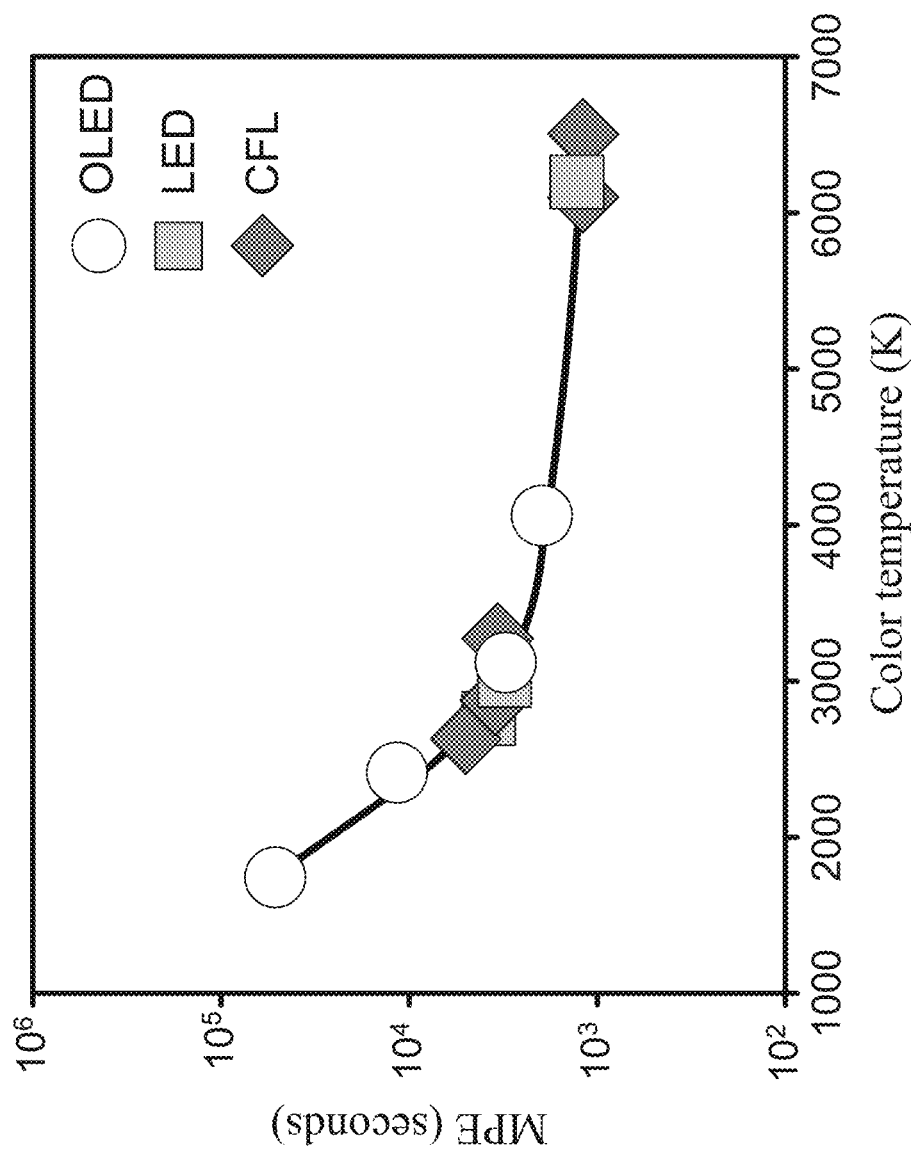
FIG. 7 shows a scatter plot of color temperature versus MPE.

Moreover, FIG. 7 shows a scatter plot of color temperature versus MPE. The experimental data of FIG. 7 are obtained from four OLED lighting elements, four compact fluorescent (CFL) lamps, and three LED lighting elements, and are recorded in following Table (2). From the experimental data of FIG. 7 and Table (2), it is found that the eleven light sources emit eleven different lights. Moreover, the MPE of each of the eleven different lights is more and more shortened with the increase of the color temperature.

TABLE 2

| Light source | Color temperature (K) | MPE (second) |
| --- | --- | --- |
| OLED-1 | 1742 | 1159400 |
| OLED-2 | 2480 | 259920 |
| OLED-3 | 3108 | 70380 |
| OLED-4 | 4058 | 44235 |
| CFL-1 | 2636 | 110475 |
| CFL-2 | 2875 | 77355 |
| CFL-3 | 6097 | 265275 |
| CFL-4 | 6505 | 26370 |
| LED-1 | 2758 | 84780 |
| LED-2 | 3000 | 70852 |
| LED-3 | 6193 | 28980 |

Second Embodiment

Figure 8:
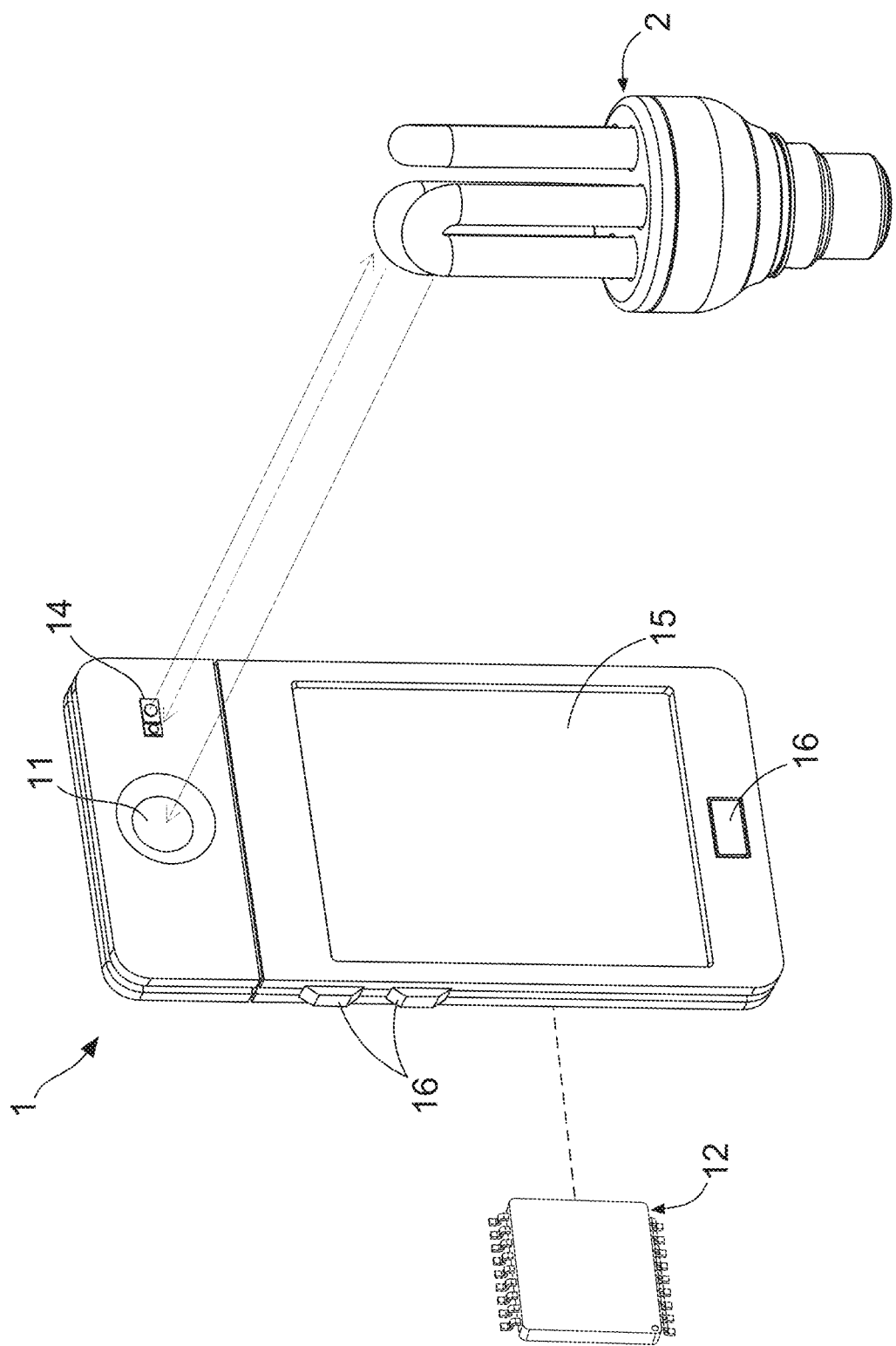
FIG. 8 shows a stereo diagram of a second embodiment of the device for simply determining MPE.
Figure 9:
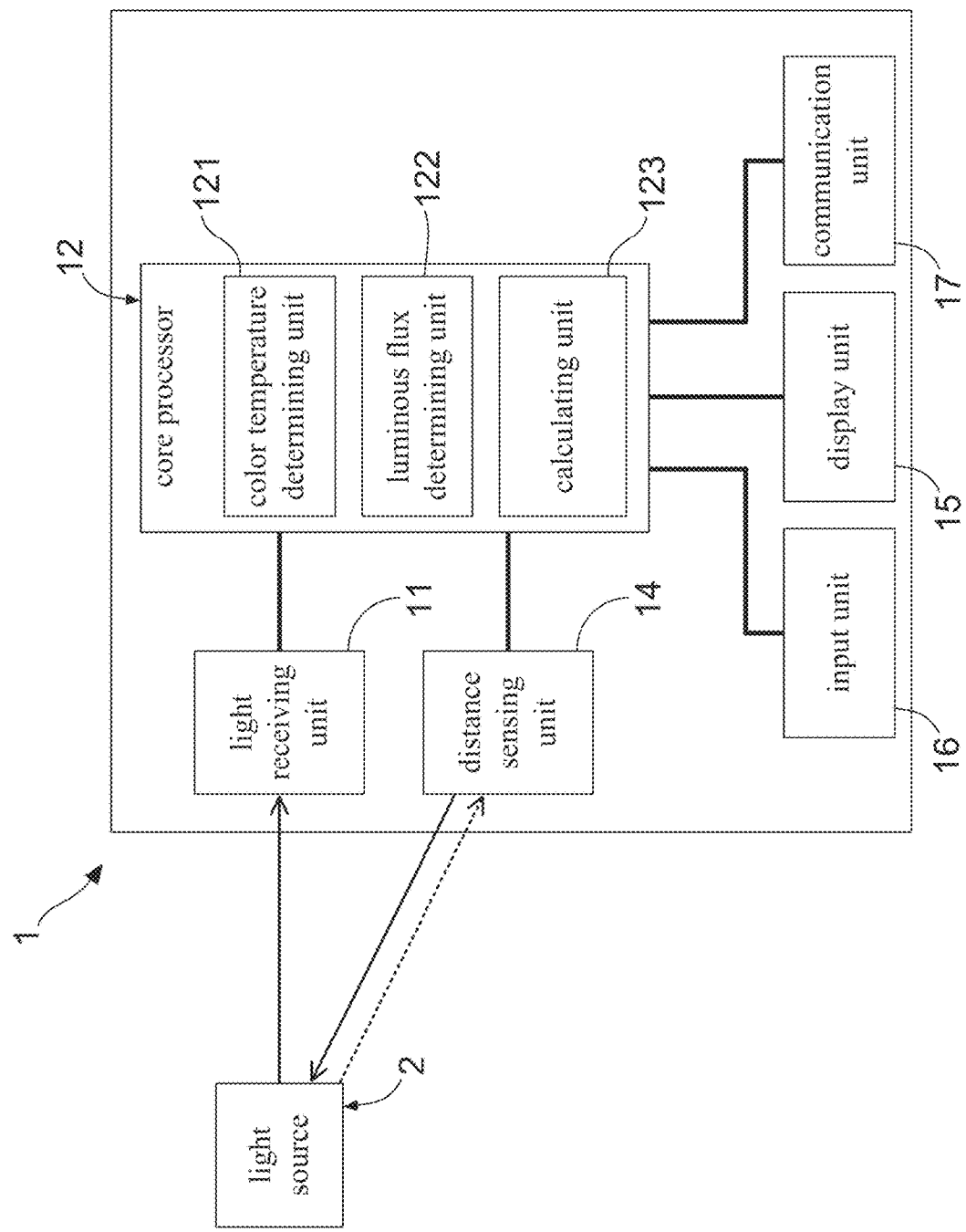
FIG. 9 shows a block diagram of the second embodiment of the device for simply determining MPE.

With reference to FIG. 8, there is shown a stereo diagram of a second embodiment of a device for simply determining maximum permissible exposure time (MPE) of retina according to the present invention. Moreover, FIG. 9 illustrates a block diagram of the second embodiment of the device for simply determining MPE. By comparing FIG. 9 with FIG. 4, it is understood that, the second embodiment of the device 1 of the present invention further comprises a distance sensing unit 14, which is coupled to the core processor 12 for being used to detect a sensing value of the use distance. Briefly speaking, in the above-described first embodiment of the device 1, a user is required for inputting the use distance between the light receiving unit 11 and the light source 2 through the input unit 16. Differently, in the second embodiment, the use distance is measured by the distance sensing unit 14 so as to further transmit to the core processor 12. In a practicable embodiment, the distance sensing unit 14 comprises a data processor and a distance sensor that is selected from the group consisting of optical distance sensor, ultrasonic distance sensor, and radar distance sensor.

Therefore, through above descriptions, all embodiments and their constituting elements of the device and for simply determining maximum permissible exposure time of retina proposed by the present invention have been introduced completely and clearly; in summary, the present invention includes the advantages of:

(1) The present invention discloses a device for simply determining maximum permissible exposure time (MPE) of retina. The device principally comprises a light receiving unit 11 and a core processor 12. Particularly, there are a color temperature determining unit 121, a luminous flux determining unit 122 and a calculating unit 123 provided in the core processor 12. After the light receiving unit 11 receives a light from a light source 2, the color temperature determining unit 121 and the luminous flux determining unit 122 complete a color temperature determination and a luminous flux determination of the illumination light, respectively. After that, the calculating unit 123 is able to consequently calculate a maximum permissible exposure time (MPE) of retina of the light source 2 based on a use distance, a value of color temperature transmitted from the color temperature determining unit 121 and a value of luminous flux received from the luminous flux determining unit 122.

As such, by using this novel device, generic users are facilitated to achieve the calculation of any one kind of light's MPE by themselves, without needing to collect spectrum data, and also without needing to look up a blue-light hazard function in order to obtain corresponding spectral weighting value.

The above description is made on embodiments of the present invention. However, the embodiments are not intended to limit scope of the present invention, and all equivalent implementations or alterations within the spirit of the present invention still fall within the scope of the present invention.

What is claimed is:

1. A device for simply determining maximum permissible exposure time of retina, comprising:
    a light receiving unit, being used for receiving a specific light that is irradiated from a light source, wherein there is a use distance between the light receiving unit and the light source; and
    a core processor, being coupled to the light receiving unit for receiving the specific light, and comprising:
        a color temperature determining unit for completing a color temperature determination of the specific light;
        a luminous flux determining unit for carrying out a luminous flux determination of the specific light; and
        a calculating unit, being configure for calculating a maximum permissible exposure time (MPE) of the specific light based on the use distance and a color temperature and a luminous flux of the specific light.

2. The device of claim 1, wherein the calculating unit comprises a mathematical algorithm for completing a calculation of the MPE, and the mathematical algorithm being presented as $$MPE\left(\frac{F_L}{D}\right) = J + K\left(e^{\frac{-T}{L}}\right) + M\left(e^{\frac{-T}{N}}\right);$$

wherein MPE is the maximum permissible exposure time, $F_L$ being the luminous flux, D being the use distance, T being the color temperature, and J, K, L, M, and N being statistical experience constants.

3. The device of claim 1, further comprising a distance sensing unit, being coupled to the core processor, and being used for detecting a sensing value of the use distance.

4. The device of claim 1, wherein the color temperature determining unit, the luminous flux determining unit and the calculating unit are provided in the core processor by a form of firmware, function library, application program, or operands.

5. The device of claim 1, further comprising:
    a display unit, being coupled to the core processor, thereby being controlled by the core processor so as to display the use distance, the color temperature, the luminous flux, and/or the MPE;
    an input unit, being coupled to the core processor, such that a user is facilitated to input the use distance to the core processor; and
    a communication unit, being coupled to the core processor, such that the core processor is able to communicate with an external electronic device through the communication unit.

6. The device of claim 1, wherein the device is an electronic device selected from the group consisting of desk optical measuring instrument, portable optical measuring instrument, smartphone integrated with optical measuring unit, smartphone connected with external optical measuring module, tablet PC integrated with optical measuring unit, tablet PC connected with external optical measuring module, laptop computer integrated with external optical measuring unit, laptop computer connected with external optical measuring module, all-in-one desktop computer integrated with optical measuring unit, all-in-one desktop computer connected with external optical measuring module, and desktop computer connected with external optical measuring module.

7. The device of claim 3, wherein the distance sensing unit comprises a data processor and a distance sensor that is selected from the group consisting of optical distance sensor, ultrasonic distance sensor, and radar distance sensor.

8. The device of claim 5, wherein the display unit is a touch screen display device, and the input unit comprising a plurality of key presses.

9. The device of claim 5, wherein the communication unit comprises a wired transmission interface and/or a wireless transmission interface.

10. A method for simply determining maximum permissible exposure time of retina, comprising:
  (1) letting a core processor be coupled to a light receiving unit;
  (2) letting the light receiving unit receive a specific light that is irradiated from a light source, wherein there is a use distance between the light receiving unit and the light source;
  (3) configuring a color temperature determining unit and a luminous flux determining unit in the core processor, so as to complete a color temperature determination and a luminous flux determination of the specific light; and
  (4) configuring a calculating unit in the core processor, so as to carry out a calculation of a maximum permissible exposure time (MPE) of the specific light based on the use distance and a color temperature and a luminous flux of the specific light.

11. The method of claim 10, further comprising:
  (5) letting the core processor be coupled to a display unit, so as to control the display unit to show the use distance, the color temperature, the luminous flux, and/or the MPE.

12. The method of claim 10, wherein the color temperature determining unit, the luminous flux determining unit and the calculating unit are provided in the core processor by a form of firmware, function library, application program, or operands.

13. The method of claim 10, wherein the calculating unit comprises a mathematical algorithm for completing a calculation of the MPE, and the mathematical algorithm is presented as $$MPE\left(\frac{F_L}{D}\right) = J + K\left(e^{\frac{-T}{L}}\right) + M\left(e^{\frac{-T}{N}}\right);$$

wherein MPE is the maximum permissible exposure time, $F_L$ being the luminous flux, D being the use distance, T being the color temperature, and J, K, L, M, and N being statistical experience constants.

14. The method of claim 10, being applied in an electronic device that is selected from the group consisting of desk optical measuring instrument, portable optical measuring instrument, smartphone integrated with optical measuring unit, smartphone connected with external optical measuring module, tablet PC integrated with optical measuring unit, tablet PC connected with external optical measuring module, laptop computer integrated with external optical measuring unit, laptop computer connected with external optical measuring module, all-in-one desktop computer integrated with optical measuring unit, all-in-one desktop computer connected with external optical measuring module, and desktop computer connected with external optical measuring module.

15. The method of claim 10, wherein the use distance is inputted to the core processor by using an input unit.

16. The method of claim 10, wherein the use distance is measured by a distance sensing unit that comprises a data processor and a distance sensor.

17. The method of claim 11, wherein the display unit is a touch screen display device.

18. The method of claim 16, wherein the distance sensor is selected from the group consisting of optical distance sensor, ultrasonic distance sensor, and radar distance sensor.

* * * * *